United States Patent [19]

Kamiya et al.

[11] Patent Number: 5,487,788
[45] Date of Patent: Jan. 30, 1996

[54] METHOD FOR CLEANING AND DISINFECTING CONTACT LENS

[75] Inventors: Hideaki Kamiya, Gifu; Satoshi Hashimoto; Satoru Matumoto, both of Nagoya, all of Japan

[73] Assignee: Tomei Sangyo Kabushiki Kaisha, Nagoya, Japan

[21] Appl. No.: 239,887

[22] Filed: May 9, 1994

Related U.S. Application Data

[63] Continuation-in-part of Ser. No. 41,203, Apr. 1, 1993.

[30] Foreign Application Priority Data

Apr. 3, 1992 [JP] Japan .................................. 4-82215

[51] Int. Cl.$^6$ ................................................ B08B 3/10
[52] U.S. Cl. ...................................... 134/1; 134/2; 134/3
[58] Field of Search ........................... 134/1, 3, 19, 27, 134/29, 30, 84, 2

[56] References Cited

U.S. PATENT DOCUMENTS

| | | |
|---|---|---|
| 2,898,282 | 8/1959 | Flook, Jr. et al. . |
| 4,202,740 | 5/1980 | Stoner et al. . |
| 4,384,943 | 5/1983 | Stoner et al. ........................ 204/149 |
| 4,396,583 | 8/1983 | LeBoeuf . |
| 4,568,517 | 2/1986 | Kaspar et al. . |
| 4,732,185 | 3/1988 | Cowle et al. . |
| 4,761,208 | 8/1988 | Gram et al. . |
| 4,836,859 | 6/1989 | Konishi et al. . |
| 4,839,004 | 6/1989 | Castellini . |
| 4,921,544 | 5/1990 | Cowle et al. . |
| 4,954,263 | 9/1990 | Woodhouse . |
| 5,118,401 | 6/1992 | Oksman et al. ........................ 204/228 |
| 5,129,999 | 7/1992 | Holland et al. . |
| 5,135,623 | 8/1992 | Dziabo et al. . |
| 5,246,552 | 9/1993 | Kamiya et al. ........................ 204/131 |

FOREIGN PATENT DOCUMENTS

| | | |
|---|---|---|
| 56-68454 | 6/1981 | Japan . |
| 57-153653 | 9/1982 | Japan . |
| 60-7060 | 3/1985 | Japan . |
| 60-217333 | 10/1985 | Japan . |
| 63-35023 | 3/1988 | Japan . |
| 63-193129 | 8/1988 | Japan . |
| 3-171032 | 7/1991 | Japan . |
| 89/00430 | 1/1989 | WIPO . |

*Primary Examiner*—Jan H. Silbaugh
*Assistant Examiner*—Robin S. Gray
*Attorney, Agent, or Firm*—Armstrong, Westerman Hattori, Mc Leland & Naughton

[57] ABSTRACT

A method of cleaning and disinfecting a contact lens comprising immersing a contact lens in a treating solution, applying a direct current to the treating solution with repeatedly reversing a positive electrode and a negative electrode of a pair of electrodes plural times to generate peroxide and raise the temperature of the treating solution so that the interval of time before reversing is different from or equal to the interval of time after reversing to 50° to 100° C., and bringing the contact lens into direct contact with bubbles generated on the electrodes. Since this method is excellent in electrical safety and cleaning and disinfecting effects, contact lenses can be easily cleaned and disinfected.

4 Claims, 5 Drawing Sheets

METHOD FOR CLEANING AND DISINFECTING CONTACT LENS

CROSS-REFERENCE TO RELATED APPLICATION

This is a continuation-in-part of application Ser. No. 041,203 filed on Apr. 1, 1993.

BACKGROUND OF THE INVENTION

The present invention relates to a method for cleaning and disinfecting a contact lens comprising immersing a contact lens in a treating solution and applying an electric current directly to the treating solution.

A contact lens has some apprehensions that eyes are injured when the contact lens is continuously worn in eyes as it is for a long period of time because stains in the surroundings, microbes, proteins contained in tear fluid, and the like adhere to the contact lens while the contact lens is worn in eyes. Accordingly, there is a necessity to clean or disinfect the contact lens regularly, preferably every day.

As a method for cleaning a contact lens, a method comprising washing the contact lens with a solution containing a surface active agent by fingers has been conventionally known. According to this method, stains on the surface of the contact lens can be removed. However, for instance, when the method is applied to a hard contact lens, there is an apprehension that the hard contact lens is broken or takes scratches during washing. Also, when the method is applied to a water-absorptive soft contact lens, stains such as proteins, which have gotten into the interior of the contact lens, cannot be completely removed. Also, when the water-absorptive soft contact lens is boiled to disinfect in a state that the stains such as proteins, which have gotten into the interior of the lens, are not completely removed, denaturation or coagulation of the proteins having gotten into the contact lens proceeds, and denatured proteins or coagulated proteins are more stiffly adhered to the contact lens. As a result, there occurs a problem of generation of cloudiness of the contact lens.

As a cleaning agent for a contact lens stained with proteins, a cleaning agent containing a proteolytic enzyme has been conventionally known. However, when this cleaning agent is used, although proteins adhered to the surface of the contact lens can be decomposed, it takes a long period of time to obtain cleaning effects. Especially, when the water-absorptive soft contact lens is cleaned by using the cleaning agent, besides taking a long period of time for treating the water-absorptive soft contact lens in comparison with the period of time for treating a hard contact lens, sufficient removing effects of proteins cannot be expected because the proteolytic enzyme itself should go into the interior of a contact lens so that proteins being denatured in the interior of the contact lens can be decomposed.

U.S. Pat. No. 4,732,185 discloses a method for cleaning a contact lens comprising establishing an electric field in a determined direction in a boric acid-EDTA buffer solution having pH 8 to 9 and immersing a contact lens in the solution to remove proteins from the contact lens by electrophoresis. When this method is carried out, proteins contaminated in the interior of a water-absorptive contact lens can be surely removed. However, the method requires that proteins should not be denatured and are ionized, and there are some problems in the method such that it takes a long period of time for the treatment. Also, according to this method, there are some problems such that a contact lens cannot be heated to prevent the thermal denaturation of proteins, and that boric acid does not impart suffient disinfecting effect to the contact lens.

U.S. Pat. No. 5,118,401 discloses a counter periodically changes the logical level of its output signal at 8 times during the disinfection cycle when an apparatus for applying a disinfectant solution containing 0 to 5% of hydrogen peroxide. However, when the content of hydrogen peroxide is 0% or so, disinfecting effects are not sufficiently imparted to a contact lens. Also, when hydrogen peroxide is used in the disinfectant solution, there is a problem such that strong stimulation is imparted to human skin.

On the other hand, as a method for disinfecting a water-absorptive contact lens, a method comprising immersing the contact lens in a sodium chloride aqueous solution and generating hypochlorite by applying an electric current to the solution to disinfect the contact lens as disclosed in Japanese Unexamined Patent Publication No. 68454/1981 and Japanese Unexamined Patent Publication No. 153658/1982, a method comprising immersing a contact lens in an $H_2O_2$ aqueous solution to disinfect the contact lens and decomposing the $H_2O_2$ with a metallic catalyst, a reducing agent and an enzyme catalyst to make the solution harmless as disclosed in Japanese Unexamined Patent Publication No. 38559/1983, Japanese Unexamined Patent Publication No. 68858/1985 and Japanese Unexamined Patent Publication No. 217333/1985, and the like have been known other than the above-mentioned method for disinfecting a contact lens comprising boiling the contact lens to disinfect.

However, according to the method of generating hypochlorite (a hypohalite) by electrolysis, it takes a long period of time for the natural disappearance of hypochlorite remaining in a treating vessel after disinfecting, and the procedures are also complex because the hypochlorite should be reduced so that hypochlorite does not remain in a water-absorptive contact lens. Furthermore, when the above procedures are applied to a colored contact lens or a dye-marked contact lens, there are some problems such that decoloration or discoloration of the contact lens occurs during the treatment.

Also, according to the above-mentioned method of using an $H_2O_2$ aqueous solution, besides taking a long period of time for the treatment since $H_2O_2$ remaining in the water-absorptive soft contact lens should be decomposed, stimulation such as smarting of eyes occurs if $H_2O_2$ remaining in the interior of the water-absorptive contact lens is not completely decomposed. Therefore, the above method is not a suitable disinfecting method.

In consideration of the problems of the above-mentioned prior art, a method for solving the problems has been found (Japanese Patent Application No. 114463/1990).

This method is a method for cleaning and disinfecting a contact lens, comprising immersing a soft contact lens electrolyte solution in which a hypohalogenous acid salt is not generated by electrolysis, and applying a direct current to the solution to remove protein from the surface of the contact lens and/or the interior thereof, and at the same time increasing the temperature of the treating solution to a temperature within the range of 80° to 100° C. to heat and disinfect the contact lens. More concretely, the above-mentioned method utilizes the electrophoresis, that is, the nature that a colloidal, electrically charged protein is moved from the contact lens to an anode or cathode by applying a direct current to the electrolyte solution when the protein is not denatured and is liberated in the electrolyte solution. This method comprises cleaning a contact lens by moving protein adhered to or existing inside of the contact lens, which is immersed in the electrolyte solution, to the outside of the contact lens, and decomposing and removing the protein with the aid of peroxide generated by the electrode reaction, and at the same time heating the electrolyte solution to a temperature of 80° to 100° C. and disinfecting the contact lens with the aid of the application of electric current.

However, the upper limit of the concentration of peroxide generated in the above-mentioned method is at most 2 to 3 ppm, and the concentration is lowered within 5 minutes from the beginning of the application of electric current. Therefore, with many stains such as protein which is denatured and adhered to the contact lens, cleaning effect becomes sometimes insufficient.

In recent years, since a domestic power source for boiling and disinfecting a water-absorptive soft contact lens and the like cannot be sometimes used while traveling, the development of a method for easily disinfecting and cleaning a contact lens using a little electric power has been desired.

The present invention has been accomplished in consideration of the above prior art.

An object of the present invention is to provide a method which can easily, effectively and safely clean a contact lens.

Another object of the present invention is to provide a method of cleaning a contact lens, giving no wrong influences to eyes, having safety for eyes and excellent detergency, by which protein which is adhered to or existed in the interior of the contact lens can be removed.

A further object of the present invention is to provide a method for cleaning and disinfecting a contact lens for which only a low electric power is required from the viewpoint of electric safety.

A still further object of the present invention is to provide a method for electrically treating a contact lens, which can be preferably applied to a portable contact lens treating apparatus by using a battery.

These and other objects of the present invention will become apparent from the description hereinafter.

SUMMARY OF THE INVENTION

In accordance with the present invention, there is provided a method for cleaning and disinfecting a contact lens comprising the steps of:

A. immersing a contact lens in a treating solution selected from the group consisting of boric acid salt buffer solution, phosphoric acid salt buffer solution, citric acid salt buffer solution, acetic acid salt buffer solution, oxalic acid salt buffer solution, succinic acid salt buffer solution, tartaric acid salt buffer solution, an aqueous solution containing a treating agent of which main components are boric acid and borax, $Na_2SO_4$ aqueous solution and admixture thereof, B. applying a direct current to the treating solution with repeatedly reversing a positive electrode and a negative electrode of a pair of electrodes plural times so that the interval of time before reversing is different from or equal to the interval of time after reversing to generate peroxide and raise the temperature of the treating solution to 50° to 100° C., and C. bringing the contact lens into direct contact with bubbles generated on the electrodes.

DETAILED DESCRIPTION

In accordance with the present invention, there is employed a method comprising immersing a contact lens in a treating solution (electrolyte solution) and applying a direct current to the treating solution with repeatedly reversing a positive electrode and a negative electrode of a pair of electrodes with each other at a predetermined period of time. In this method, the interval of period of time before or after reversing is discretionary. It is preferable that the difference between the interval before and after reversing is great for increasing the effects based upon electrophoresis.

In accordance with the method of the present invention, a great amount of peroxide is surprisingly generated. The amount of the generated peroxide is about 5 to about 10 times the amount of peroxide generated in a conventional method comprising applying a direct current to an electrolyte solution without reversing a positive electrode and a negative electrode during the treatment. Thus, when the amount of generated peroxide is great, the disinfecting effect based upon not only increased temperature but also the peroxide itself is improved.

Also, in accordance with the method of the present invention, protein can be effectively removed from a contact lens in a very short period of time, with the aid of the function of D.C. electric field which moves the protein to the outside of the contact lens, and the function of effectively solubilizing the protein in the treating solution with the aid of peroxide generated by the electrode reaction.

Moreover, in the present invention, since the peroxide is almost completely disappeared without remaining in the contact lens when the treatment is finished, complicated procedures such as reduction are not necessitated.

Accordingly, the contact lens can be cleaned and disinfected by merely immersing the contact lens the treating solution and applying a direct current to the treating solution, and after that, the contact lens can be worn in eyes as it is.

The mechanism of decomposition of the protein is not clear. It is thought that the peroxide acts on an amide to cleave peptide bonds of the protein like hydrolysis.

Also, as mentioned above, when a direct current is applied to the treating solution with repeatedly reversing a positive electrode and a negative electrode of a pair of electrodes plural times at a predetermined interval of time, the amount of generated peroxide becomes as about 5 to about 10 times as the amount of peroxide generated in a method comprising applying a direct current to the treating solution without reversing the polarity of electrodes. However, its reason is not clear. It is supposed that although some peroxides are disappeared during the repeated reverse of electrodes, the amount of the peroxides generated becomes greater than the disappeared amount of the peroxides, and the peroxides are probably dispersed in the treating solution by electric repulsion during the reverse of the electrodes.

As the peroxides which are generally generated by electrolysis on electrodes, for instance, hydrogen peroxide, ozone and the like are cited.

Examples of the treating solution are, for instance, boric acid salt buffer solution, phosphoric acid salt buffer solution, citric acid salt buffer solution, acetic acid salt buffer solution, oxalic acid salt buffer solution, succinic acid salt buffer solution, tartaric acid salt buffer solution, an aqueous solution containing a treating agent of which main components are boric acid and borax, $Na_2SO_4$ aqueous solution and admixture thereof. These treating solutions can be used alone or in admixture thereof. Among them, from the viewpoint of not affecting wrong influences to the material, standard and shape of the contact lens, and safety for eyes even when the treating solution is accidentally into eyes, treating solutions such as phosphoric acid salt buffer solution, acetic acid salt buffer solution, citric acid salt buffer solution and boric acid salt buffer solution are particularly preferable.

It is desired that the concentration of an electrolyte in the treating solution is 0.001 to 0.5 mol/l, preferably 0.05 to 0.2 mol/l, more preferably 0.1 to 0.2 mol/l. When the concentration is less than the above range, there is a tendency that high voltage should be applied to the solution so that an electric current is adjusted to generate peroxides. Also, when the concentration exceeds the above range, in case of cleaning and disinfecting a contact lens, the osmotic pressure of the treating solution becomes too high, and thereby the size of the contact lens is deformed and there is a tendency that eyes are stimulated when the contact lens is treated with the treating solution and then the treated contact lens is worn in eyes as it is.

Also, since the electric charge of proteins contained in the treating solution is changed by the pH of the treating solution, the proteins sometimes do not move at all when applying an electric current to the treating solution according to the pH of the treating solution. At that time, the pH is called as an isoelectric point (hereinafter referred to as pI) of the proteins. It is desirable that the pI of the treating solution used in the present invention is essentially different from pI of protein for the sake of revelation of effects. For instance, it is desirable that each pI of the proteins, which are main constituting components of a tear fluid, such as albumin (pI 4.7 to 5.0), globulin (pI 5.2 to 5.4) and lysozyme (pI 10.5 to 11.4) is different from that of the treating solution. That is, it is desirable that the treating solution has pH 1 to 4.6, pH 5.5 to 10.4 or pH 11.5 to 14. Further, in consideration of wrong influences to the material of a contact lens and safety for eyes when the contact lens is taken out from the treating solution after the treatment and then the contact lens is worn in eyes as it is, it is desirable that the treating solution has preferably pH 5.5 to 8, more preferably pH 6 to 7.5.

Furthermore, in the present invention, one or more compound selected from urea, thiocyanic acid salts and compounds having reducing properties can be contained in the above-mentioned treating solution.

These compounds are the components for easily removing proteins existing in the contact lens, particularly denatured proteins which cannot be removed by usual electrophoresis. The function and amount of urea and thiocyanic acid salts are different from those of the compounds having reducing properties as mentioned later.

In general, urea and thiocyanic acid salts are the components having a function to heighten the water solubility of low molecular nonelectrolytes, proteins and the like. According to the present invention, proteins adhered to the surface of the contact lens or proteins immanent in the contact lens are efficiently removed by the multiplier action of the above function and removing function of proteins based upon electrophoresis and peroxides produced by electrode reaction.

There is generally a necessity to adjust the concentration of urea and/or thiocyanic acid salts in the treating solution to be relatively high such as 0.5 to 4 mol/l or so for sufficiently cleaning the contact lens. However, according to the present invention, since the multiplier action based upon generated peroxides and the like is exhibited as mentioned above, the concentration can be lowered to at most 0.5 mol/l, more preferably 0.01 to 0.5 mol/l, particularly preferably 0.04 to 0.06 mol/l or so. Also, it is preferable to adjust the concentration to at least 0.01 mol/l so that the urea and/or thiocyanic acid salts can show the removing effect of proteins. Even when the concentration is lower than the above range, stains of proteins, which are adhered to the contact lens while the contact lens is worn in eyes, can be removed by the peroxides. Also, when the above concentration exceeds the above range, the removing effect of proteins is improved. However, in case of cleaning and disinfecting a soft contact lens, eyes smart with a contact lens when the contact lens is treated with the solution and then is worn in the eyes as it is since the osmotic pressure of the treating solution becomes relatively high. Also, when a hard contact lens is cleaned and disinfected in an excessively concentrated treating solution, the hard contact lens should be sometimes sufficiently washed after cleaning.

As mentioned above, in the present invention, when urea and/or thiocyanic acid salts are used, since these can be used in a lower concentration, a water-absorptive contact lens would not be swollen or shrunk, and there is no necessity to wash the water-absorptive contact lens sufficiently after cleaning like a high concentration solution.

Examples of the thiocyanic acid salts are, for instance, ammonium thiocyanate, sodium thiocyanate, potassium thiocyanate, calcium thiocyanate, and the like. These can be used alone or in admixture thereof.

The compounds having reducing properties which can be used in the present invention have a nature for reducing intermolecular or intramolecular S-S bonds of proteins adhered to the surface of the contact lens or proteins immanent in the contact lens. When the compounds having reducing properties are used, it is desirable that its concentration in the treating solution is adjusted to usually at most 0.1 mol/l, preferably 0.005 to 0.05 mol/l. When the concentration exceeds the above range, removing effects of proteins are improved. However, in case of cleaning and disinfecting the contact lens, since the osmotic pressure of the treating solution becomes relatively high, there is a tendency that the size of a treated contact lens is sometimes changed and eyes sometimes smart with a treated contact lens when the treated contact lens is worn in eyes as it is after the treatment.

Examples of the above-mentioned compounds having reducing properties are, for instance, thiosulfuric acid alkali metal salts or thiosulfuric acid alkaline earth metal salts such as sodium thiosulfate, potassium thiosulfate and calcium thiosulfate; sugars such as D-glucose, L-glucose, lactose and D-fructose; cysteine; methionine; acids, or alkali metal salts or alkaline earth metal salts thereof such as sorbic acid, potassium sorbate, citric acid and sodium citrate; sulfurous acid salts such as sodium sulfite, potassium sulfite and sodium hydrogen sulfite; ascorbic acid; glutathione and the like. These compounds having reducing properties can be used alone or in admixture thereof.

Also, according to the present invention, as mentioned above, urea, thiocyanic acid salts and compounds having reducing properties are usually used alone or in admixture thereof. When urea and/or thiocyanic acid salts, and the compounds having reducing properties are simultaneously used, each amount of these can be within a range mentioned above, respectively.

Among the above-mentioned compounds having reducing properties, when the compounds having reducing properties, which have strong reducing power, such as a thiosulfuric acid salt and a sulfurous acid salt are used, the removing effect of protein can be improved. However, on the other hand, peroxide generated by the electrode reaction is reduced, and the disinfecting effect is sometimes lowered. Accordingly, it is preferable that citric acid or sodium citrate, which has a relatively small reducing power, is used as the compounds having reducing properties.

The treating solution for articles to be cleaned such as contact lenses used in the present invention can be an aqueous solution of the above treating agent, which is previously prepared, or a treating agent having a shape like powder, granules or pellets from which an aqueous solution is prepared by dissolving the treating agent in water when a user uses the solution.

In the present invention, the treatment of the contact lens is carried out by immersing the contact lens in the treating solution and applying a direct current to the treating solution through a pair of electrodes with repeatedly reversing a positive electrode and a negative electrode of a pair of electrodes plural times so that the interval of time before reversing is different from the interval of time after reversing to generate peroxide and raise the temperature of the treating solution to 50° to 100° C., and bringing the contact lens into direct contact with bubbles generated on the electrodes.

It is preferable to use an electrode material having a small ionization tendency because electrodes made of the material is hardly dissolved in the treating solution by electrode reaction when a positive electrode and a negative electrode are repeatedly reversed with each other with the passage of time.

Examples of the electrode material are, for instance, nobel metals such as gold and platinum, a synthetic resin or ceramic on which a noble metal such as gold or platinum is coated by plating or vacuum evaporation, and the like.

The number of reversing the positive electrode and the negative electrode during the treatment is not limited so long as the reversing is carried out plural times. It is preferable that the number of reversing is adjusted so that the interval of time for reversing can be within a range of 0.1 second to 5 minutes, particularly 2 seconds to 2 minutes. When the interval is shorter than 0.1 second, the effect of electrophoresis becomes small. On the other hand, when the interval is longer than 5 minutes, there is a tendency that the amount of generated peroxide does not become large.

It is desired that the treating period of time is 10 to 60 minutes. When the treating period of time is less than 10 minutes, the amount of peroxide generated becomes too small. On the other hand, when the treating period of time is more than 60 minutes, the time necessitated for the treating procedure becomes too long.

Also, it is desired that the reversing times of the positive electrode and the negative electrode are 9 to 320 times, preferably 15 to 160 times. When the reversing times are less than 9 times, there is a tendency that sufficient disinfecting properties are not obtained. On the other hand, when the reversing times are more than 320 times, there is a tendency that electrodes are easily damaged.

As a means for reversing the positive electrode and the negative electrode to which DC voltage is applied, a method comprising using an oscillator and a reverse circuit in which a counter frequency divider and a relay are provided, a method comprising using a relay only, and the like are cited.

The electric current applied to the treating solution is suitably selected depending upon the kind of the treating solution and the area of the electrode. It is preferable that the electric current is within 0.00 1 to 0.5 A or so. When the electric current is less than 0.001 A, peroxides are little generated in the electrolyte solution when an electric current is applied to the solution, thereby there is a tendency that the removing effects and disinfecting effects of proteins become small. When the electric current exceeds 0.5 A, the temperature of the treating solution is excessively increased, and the thermal deterioration such as deformation of a hard contact lens due to heating or the deterioration of the material of a contact lens having a high water content is caused when these contact lenses are cleaned and disinfected. Also, when the value of the electric current is excessively large, since higher voltage is necessitated for giving a desired electric current, there is a tendency that safety for electricity is lowered.

It is preferable that the DC voltage applied between the electrodes is 3 to 40 V or so. When the voltage is lower than the above-mentioned range, there is a tendency that the cleaning and disinfecting effect is not sufficiently exhibited. On the other hand, when the voltage exceeds the above-mentioned range, the temperature of the treating solution is excessively increased, and the contact lens is sometimes thermally deteriorated. Also, when the voltage is excessively high, there is a tendency that safety for electricity is lowered and electric shock, leakage of electricity and the like are sometimes caused.

The temperature of the treating solution is increased by applying an electric current to the treating solution. It is insufficient that the contact lens is disinfected only by the generated peroxide. Since the water-absorptive contact lens is disinfected not only by the generated peroxide but also by the synergism of the peroxide and the temperature, it is generally preferable that the temperature of the treating solution is 50° to 100° C., particularly 60° to 80° C.

The concentration of generated peroxide depends upon the amount of stains adhered to the contact lens. It is generally desired that the concentration of peroxide is not less than 5 ppm, preferably not less than 10 ppm in order to sufficiently remove protein from the contact lens. In the present invention, since the generated peroxide is almost completely disappeared just after the treatment, irritation of eyes and the like are not caused. The concentration of peroxide can be generally adjusted by adjusting the interval of reversing the positive electrode and the negative electrode, the value of electric current applied to the treating solution, and the like.

The method for cleaning and disinfecting the contact lens of the present invention is explained in the following. In the present invention, for instance, when the amount of the treating solution comprising boric acid salt buffer solution is 7 ml and the area of each electrode is 0.21 cm$^2$, respectively, peroxide can be generated in a concentration of at least 15 ppm by adjusting the interval of time for repeatedly reversing the positive electrode and the negative electrode to 30 seconds, adjusting the voltage to 20 to 25 V and applying electric current of 0.05 to 0.15 A to the solution. Since the concentration of the peroxide generated in the treating solution is attained to the maximum concentration after about 5 to about 20 minutes passed from the beginning of the application of electric current to the solution, it is preferable that the applying period of time of electric current is about 10 to about 60 minutes from the viewpoint of the effective disinfection and removal of protein.

Most of stains such as lipid adhered to the contact lens can be removed by heating the contact lens in the treating solution. In order to remove the stains more sufficiently, the contact lens may be cleaned in a cleaning solution containing a surface active agent before putting the article in a treating vessel or after cleaning and disinfecting the article, or a surface active agent may be contained in the above-mentioned treating solution.

Examples of the surface active agent are, for instance, anionic surface active agents such as sulfuric acid esters of higher alcohols or liquid fatty oil, alkyl ether sulfuric acid esters, alkyl sulfonates and sulfosuccinates; cationic surface active agents such as alkyl amine salts and alkyl ammonium salts; nonionic surface active agents such as alkyl ethers, alkyl phenyl ethers, polyoxypropylene ethers, alkyl ester glycerine fatty acid esters, sorbitan fatty acid esters and polyoxyethylene sorbitan fatty acid esters, and the like.

When the surface active agent is used by including in the treating agent, it is desirable that the concentration of the surface active agent in the treating solution is at most 0.1% by weight, preferably at most 0.05% by weight since if the concentration of the surface active agent is too high, excess bubbles are generated in the treating solution and sometimes flow out from the vessel during electrode reaction.

Also, when stains of proteins such as denatured proteins which are difficult to be removed are existed in the interior of a contact lens, a proteolytic enzyme can be included in the treating solution so that denatured proteins can be easily removed.

Examples of the proteolytic enzyme are, for instance, vegetable proteolytic enzymes and animal proteolytic enzymes such as papain, chymopapain, pancreatin, trypsin, chymotrypsin, pepsin, ficin, carboxypeptidase, aminopeptidase and bromelin; proteolytic enzymes derived from microbes such as Bacillus, Streptomyces bacteria and Aspergillus mold, and the like.

It is desirable that the concentration of the proteolytic enzyme in the treating solution is adjusted so that the enzyme activity of the proteolytic enzyme in the treating solution is 300 to 1000 unit/ml.

The thus cleaned and disinfected contact lens can be worn in eyes after the contact lens is taken out from the treating solution as it is or after the contact lens is cleaned with a saline or the like if components which are optionally added to the treating solution during the treatment give stimulation to eyes.

According to the present invention, since peroxide is generated by the electrolysis without generating hypohalogenous acid salts and the generated peroxide is disappeared in a short period of time after the treatment, there is no apprehension of discoloration or decoloration of a colored contact lens, and eyes are not irritated by remaining hypochlorite or peroxide, and furthermore, proteins adhered to or existing in a contact lens can be removed with excellent detergency, and at the same time the contact lens can be disinfected.

The present invention is more specifically explained by means of the following examples. However, the present invention is not limited to these examples.

Referential Examples 1 to 5 and Comparative Referential Example 1

Figure 1:
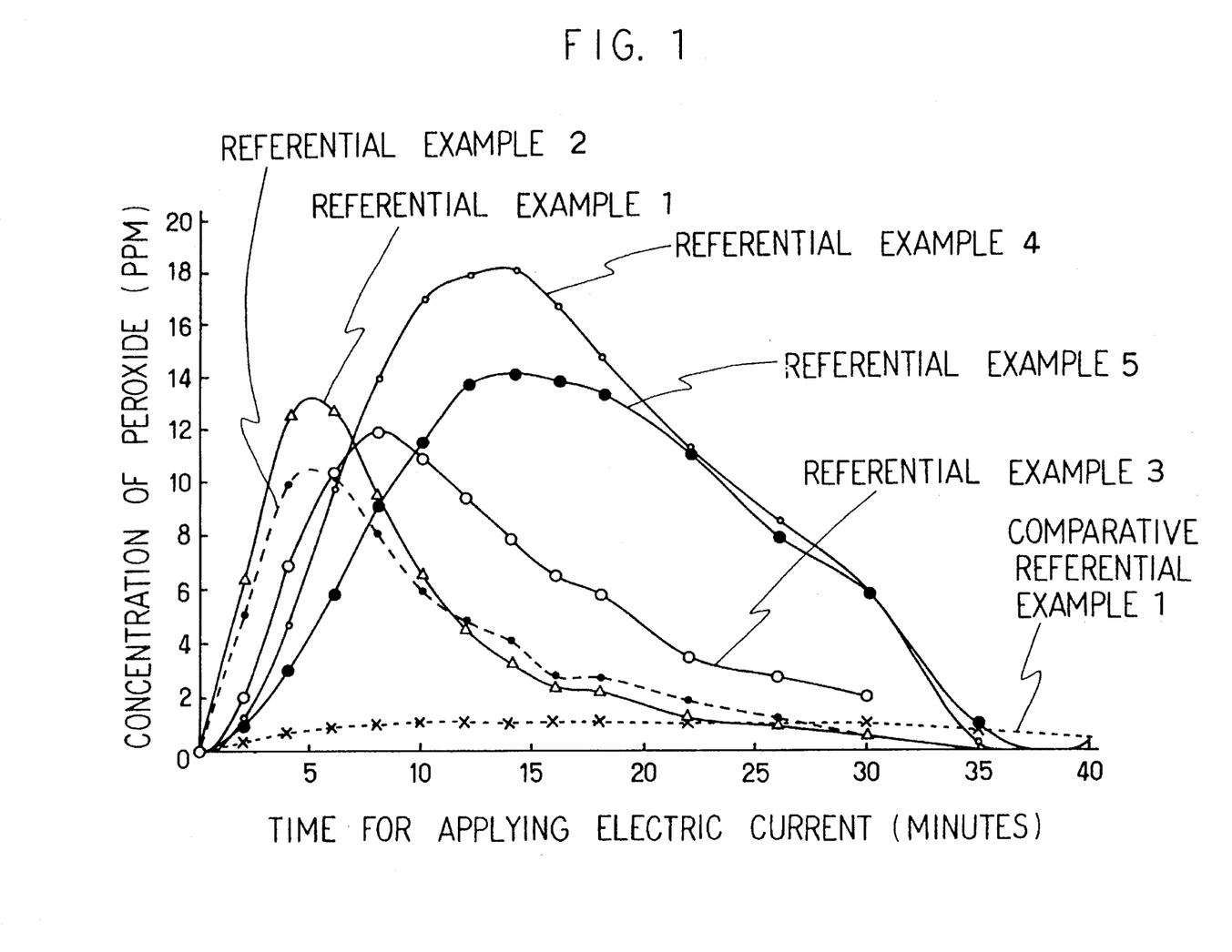
FIG. 1 is a graph showing the relation between the passage of time from the beginning of the application of electric current and the concentration of peroxide of the electrolyte solution during the application of a direct current to the electrolyte solution with repeatedly reversing a positive electrode and a negative electrode at a predetermined interval of time in Referential Examples 1 to 5 of the present invention, or during the application of a direct current to the electrolyte solution without reversing the positive electrode and the negative electrode in Comparative Referential Example 1.

To 7 ml of an electrolyte solution (pH 6.8) containing boric acid in a content of 0.21 mol/l, borax in a content of 0.00157 mol/l and trisodium citrate in a content of 0.0149 mol/l, a direct current of 25 V having an initial current of 48 mA was applied with repeatedly reversing the positive electrode and the negative electrode of a pair of electrodes at an interval of time of 3.75 seconds (Referential Example 1), 7.5 seconds (Referential Example 2), 15 seconds (Referential Example 3), 30 seconds (Referential Example 4) or 60 seconds (Referential Example 5) by using a reverse circuit, or without reversing the positive electrode and the negative electrode (Comparative Referential Example 1). The concentration of peroxide in the electrolyte solution was measured with the passage of time of the application of electric current in accordance with the following method. The results are shown in FIG. 1. The period of time for the application of electricity was 30 minutes.

(Method for measuring the concentration of peroxide)

First of all, reagents were prepared in accordance with the following method. (A) Phosphoric acid salt buffer solution: After 0.07 mole of sodium phosphate (special grade chemical) and 0.13 mole of disodium phosphate (special grade chemical) were dissolved in distilled water, and its pH was adjusted to 7.0, distilled water was added thereto to give a total amount of 1 l of a phosphoric acid salt buffer solution. (B) ABTS reagent: In the above phosphoric acid salt buffer solution, 0.113 g of 2,2'-azinobis(3-ethylbenzothiazoline-6-sulfonic acid) 2NH$_4$ salt (ABTS special grade chemical) and 100 units of PEROXIDASE Type I (commercially available from SIGMA CHEMICAL COMPANY, trade name) were dissolved to give a total amount of 100 ml of an ABTS reagent. (C) Next, after 2.0 ml of hydrogen peroxide standard solution which was diluted to at most 30 ppm and 2.0 ml of the ABTS reagent solution were admixed together and stirred, ultraviolet ray absorbance (hereinafter referred to as absorbance) was measured at 420 nm. An analytical curve was prepared by measuring the absorbance at every concentration.

Next, samples in an amount of 2.0 ml were collected from the above electric-current flowed electrolyte solution after 2, 4, 6, 8, 10, 12, 14, 16, 18, 22, 26, 30, 35 or 40 minutes passed from the beginning of the application of electric current. After each sample was mixed with 2.0 ml of the ABTS reagent solution and stirred, the absorbance at 420 nm was measured. Then, the concentration converted to a concentration of hydrogen peroxide was measured from the analytical curve.

As shown in FIG. 1, the concentration of peroxide in the electrolyte solution when reversing the positive electrode and the negative electrode was about 10 to about 20 times higher than the concentration of peroxides when not reversing the positive electrode and the negative electrode. Moreover, the concentration became almost 0 ppm after several minutes passed from the end of the application of electric current.

From the above results, it can be seen that since peroxide does not exist in the contact lens, the contact lens is safe for eyes even if the contact lens is taken out from the solution and worn in eyes as it is.

Also, it can be understood that when the treating solution is used, the interval of time for reversing the positive electrode and the negative electrode, which is suitable for giving the highest concentration of peroxide, is about 30 seconds, and when the interval is longer or shorter than about 30 seconds, there is a tendency that the concentration of peroxide is lowered.

Then, cleaning and disinfecting were carried out under the conditions that the positive electrode and the negative electrode were reversed at a different interval of time between before reversing and after reversing in accordance with the following method.

Referential Examples 6 to 9 and Comparative Referential Examples 2 to 3

To 7 ml of an electrolyte solution (pH 6.9) containing boric acid in a content of 0.0323 mol/l, borax in a content of 0.00433 mol/l, citric acid in a content of 0.0281 mol/l and trisodium citrate in a content of 0.00338 mol/l, a direct current having DC voltage of 15 V and an initial current of 0.045 A was applied with repeatedly reversing the positive electrode and the negative electrode at the interval of time of 3.75 seconds in one direction and 30 seconds in another direction (Referential Example 6), at the interval of time of 7.5 seconds in one direction and 1 minute in another direction (Referential Example 7), at the interval of time of 30 seconds in one direction and 4 minutes in another direction (Referential Example 8), at the interval of time of 30 seconds in one direction and 30 seconds in another direction (Referential Example 9) or at the interval of time of 5 minutes in one direction and 5 minutes in another direction (Comparative Referential Example 2, corresponding to the method disclosed in U.S. Pat. No. 5,118,401). The concentration of peroxide in the buffer solution was measured with the passage of time of the application of electric current. The period of time for the application of electric current was 40 minutes.

The amount of generated peroxide in repeatedly reversing the positive electrode and the negative electrode at the interval of time of 7.5 seconds in one direction and 1 minute in another direction is greater than the amount of generated peroxide in reversing the positive electrode and the negative electrode at the interval of time of 30 seconds in both directions.

In consideration of this fact and the effect of electrophoresis, it is more preferable that the method comprising repeatedly reversing the positive electrode and the negative electrode at the intervals of time, in which the interval of time before reversing is different from the interval of time after reversing. Also, according to the method of Comparative Referential Example 2, it can be understood that the amount of generated peroxide is very little.

Comparative Referential Example 3 shows that electricity was intermittently applied to the elecrolyte solution without reversing the positive electrode and the negative electrode and the period of time for the application of electric current was adjusted to 30 seconds and the period of time for the pause of the application of electric current was 3.75 seconds.

Figure 2:
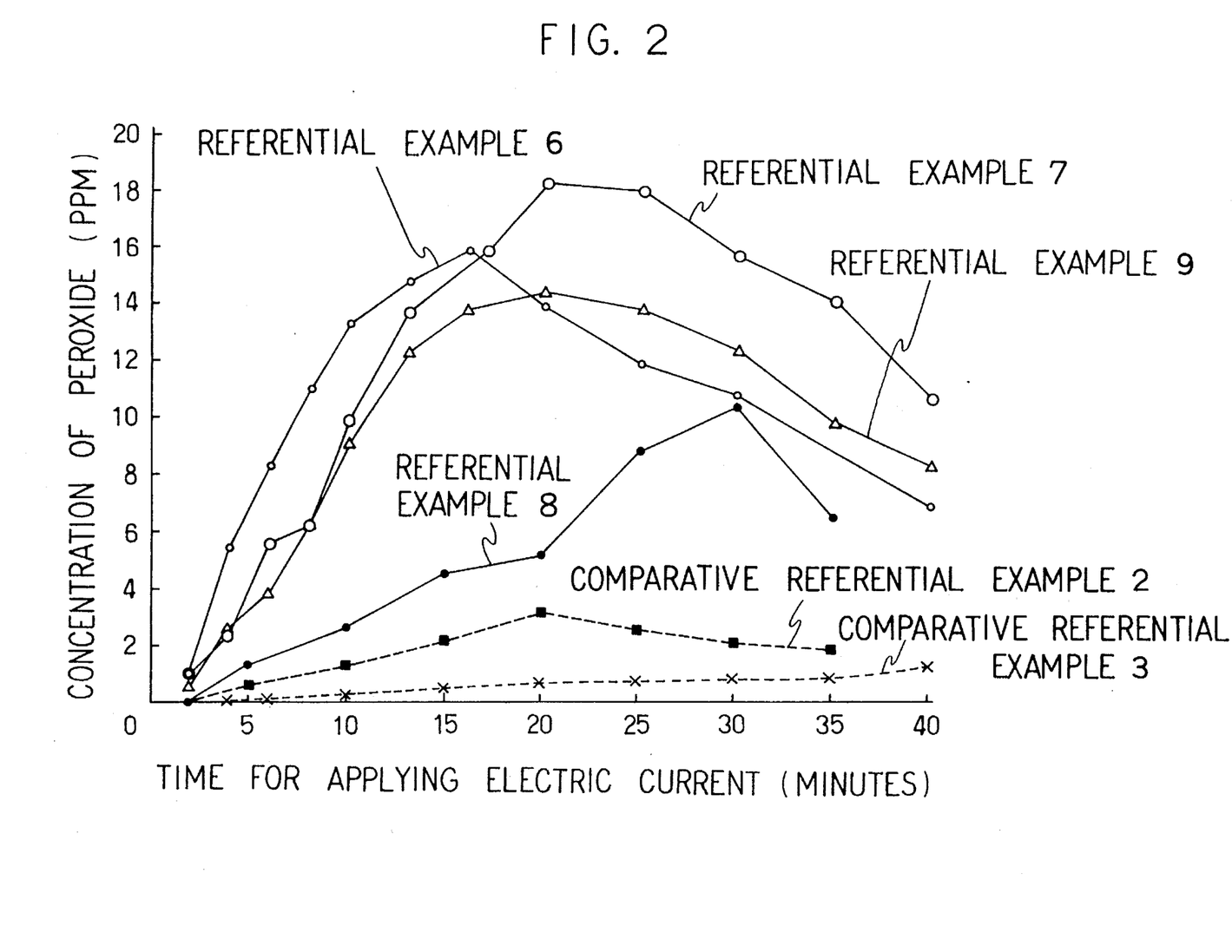
FIG. 2 is a graph showing the relation between the passage of time from the beginning of the application of electric current and the concentration of peroxide of the electrolyte solution during the application of a direct current to the electrolyte solution with repeatedly reversing a positive electrode and a negative electrode so that the interval of time before reversing differs from the interval of time after reversing in referential Examples 6 to 9 of the present invention, or during the intermittent application of a direct current to the electrolyte solution without reversing the positive electrode and the negative electrode in Comparative Referential Example 2.

From these examples, it was confirmed that little amount of peroxides was generated when the positive electrode and the negative electrode were not reversed. The results are shown in FIG. 2. The concentration of peroxides was measured after 2, 4, 6, 8, 10, 15, 20, 25, 30, 35 or 40 minutes passed from the beginning of the application of electric current.

Referential Examples 10 to 14

The concentration of peroxide in an electrolyte solution was measured in the same manner as in Referential examples 1 to 5 except that 0.2 mol/l of phosphoric acid salt buffer solution (Referential Example 10), 0.3 mol/l of boric acid salt buffer solution (Referential Example 11), 0.075 mol/l of citric acid salt buffer solution (Referential Example 12), 0.1 mol/l of sodium sulfate aqueous solution (Referential Example 13) or 0.08 mol/l of sodium hydrogencarbonate aqueous solution (Referential Example 14) was used and the voltage of 15 to 20 V having an initial current of 0.04 to 0.1 A was applied to 7 ml of the electrolyte solution.

In all of the electrolyte solutions, the concentration of peroxides which were generated by applying a direct current to the solution with repeatedly reversing the positive electrode and the negative electrode at the interval of time of about 30 seconds was the highest concentration in comparison with the concentration of peroxides which were generated only by applying a direct current to the solution from one direction. After several minutes passed from the stop of application of electric current, the concentration of peroxides became almost 0 ppm.

Referential Examples 15 to 19

As an electrolyte solution, 9.0 ml of a buffer solution formed from a 1:10 dilution of a concentrate having the following composition: 0.808 mol/l of boric acid, 0.029 mol/l of disodium edetate and 0.825 mol/l of TRIS, which is disclosed in U.S. Pat. No. 4,732,185, was used.

The concentration of peroxide in the electrolyte solution was measured when a direct current having DC voltage shown in Table 1 was applied to the electrolyte solution only in one direction. The temperature of the electrolyte solution was shown in Table 1.

Figure 3:
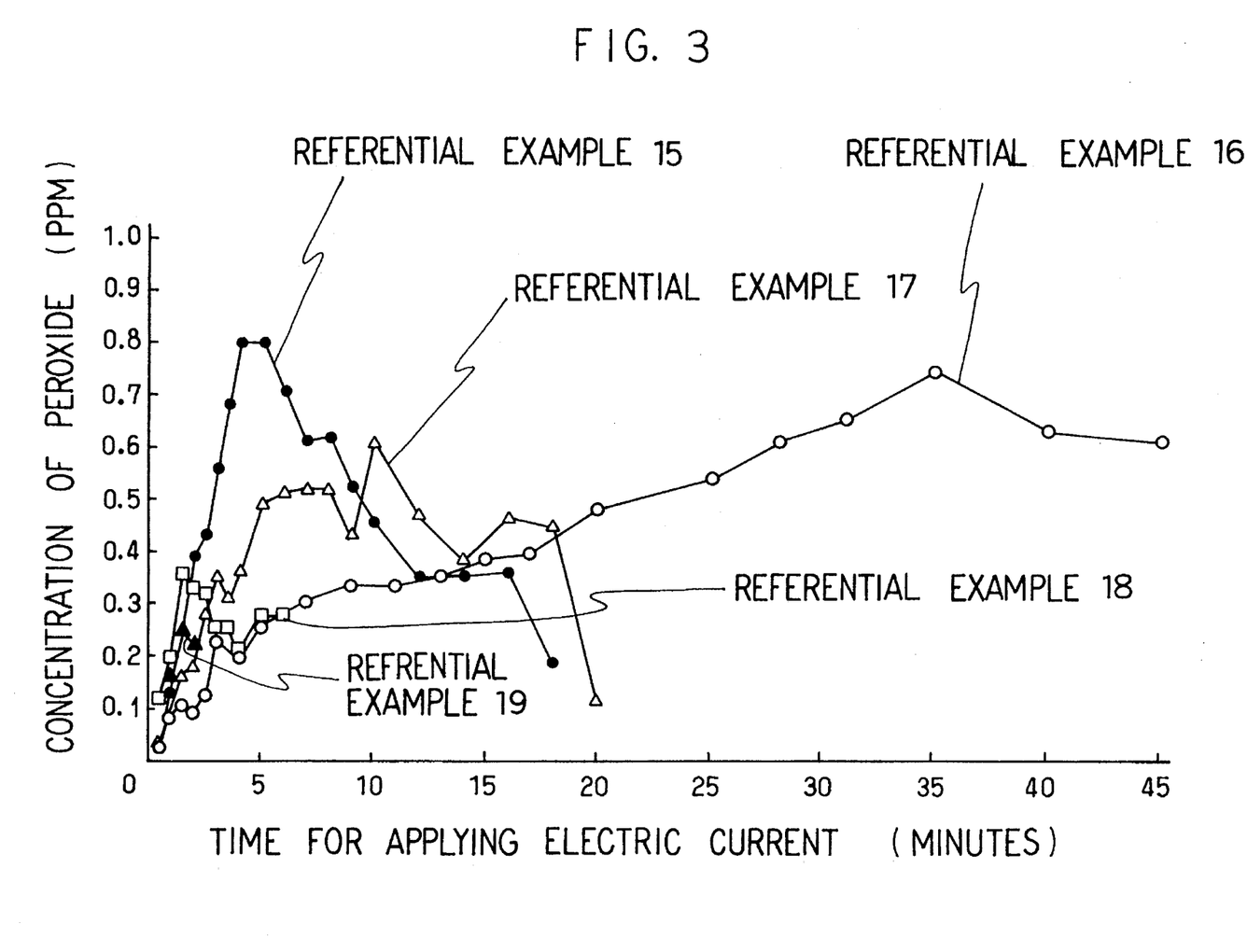
FIG. 3 is a graph showing the change of peroxide generated in an electrolyte solution with the passage of time during the application of a direct current to the electrolyte solution according to Referential Examples 15 to 19.

Also, the change of the amount of generated peroxide with the passage of time is shown in FIG. 3. As is clear from the results shown in FIG. 3, in all cases of Referential Examples 15 to 19, the concentrations of the generated peroxide were at most 1 ppm.

TABLE 1

| Referential Example No. | Voltage (V) | Current (mA) | Temperature of electrolyte solution (°C.) |
|---|---|---|---|
| 15 | 122 (Constant) | 100 (Initial value) | 100 (After 5 minutes) |
| 16 | 42 (Initial value) | 100 (Constant) | 60 (After 35 minutes) |
| 17 | 86 (Initial value) | 200 (Constant) | 85 (After 20 minutes) |
| 18 | 145 (Initial value) | 400 (Constant) | 100 (After 2 minutes) |
| 19 | 185 (Initial value) | 400 (Constant) | 100 (After 2 minutes) |

Example 1

About 1 l of an artificial tear fluid (pH 7.0) was prepared by mixing the following components.

Two soft contact lenses mainly composed of N-vinylpyrrolidone having a water content of about 70% were immersed in 1.5 ml of the artificial tear fluid at 37° C. for 16 hours to adsorb proteins in the contact lens.

| (Ingredients of the artificial tear fluid) | |
|---|---|
| Albumin | 3.88 g |
| γ-Globulin | 1.61 g |
| Lysozyme | 1.2 g |
| NaCl | 9.0 g |
| $CaCl_2.2H_2O$ | 0.15 g |
| $NaH_2PO_4.2H_2O$ | 1.04 g |
| Distilled water | 1.0 l |

After one of the contact lenses was washed by fingers with a cleaning agent for soft contact lenses "MENI CLEAN" (commercially available from Menicon Co., Ltd., trade name), the contact lens was immersed in 7 ml of a citric acid salt buffer solution (pH 6.8) containing 0.075 mol/l of trisodium citrate and 0.005 mol/l of citric acid, and voltage of 15 V having an initial electric current of 0.05 A was applied thereto. At this time, the positive electrode and the negative electrode were repeatedly reversed at the interval of time of 30 seconds using a reverse circuit. After 30 minutes passed from the beginning of the application of the electric current, the temperature of this solution attained to 75° C. During the electrolysis, the current was increased to 0.18 A. After the electric current was applied to the solution for 30 minutes, the solution was allowed to stand to cool to room temperature (22° C.).

The above procedure (from the procedure of immersing a contact lens in 1.5 ml of the artificial tear fluid to the procedure of cooling) was counted as one cycle (hereinafter referred to as cycle test $A_1$). After the cycle test $A_1$ was applied to a contact lens 100 cycles, the contact lens was observed with naked eyes. As a result, the contact lens had transparency quite equal to a contact lens to which cycle test $A_1$ was not applied.

Furthermore, the cross section of the contact lens was analyzed by an X-ray microanalyzer (commercially available from JEOL Co., under the trade name of JSM type 35) to examine the existence of sulfur after the cycle test $A_1$ was carried out 100 cycles. As a result, the existence of sulfur was not observed in the treated contact lens.

Comparative Example 1

After a soft contact lens was immersed in the above artificial tear fluid and the contact lens was washed by fingers with MENI CLEAN in the same manner as in Example 1, the contact lens was disinfected by immersing in 1.5 ml of a soaking solution for soft contact lenses "MENI SOAK" (commercially available from Menicon Co., Ltd., trade name) and using MENICON LIZER E (commercially available from Menicon Co., Ltd., trade name; hereinafter referred to as LIZER E) as an apparatus for boiling and disinfecting a soft contact lens.

The same cycle test $A_1$ as in Example 1 except that a contact lens was boiled and disinfected with LIZER E instead of the application of electric current (hereinafter referred to as cycle test $B_1$) was carried out 100 cycles. After the cycle test $B_1$ was carried out about 40 cycles, it was observed with naked eyes that the contact lens treated with LIZER E became cloudy.

The cross section of the contact lens was analyzed with an X-ray microanalyzer in the same manner as in Example 1 to observe the existence of sulfur. As a result, a peak showing the existence of sulfur was detected in the contact lens which was treated with LIZER E.

Since the contact lens material does not contain sulfur inherently, it is supposed that the detected sulfur was derived from the molecular structure of proteins, and the thermally denatured proteins caused the cloudiness of the contact lens.

On the other hand, since sulfur was not detected from the contact lens to which the cycle test $A_1$ was applied, it can be seen that the washing off of stain of protein from a contact lens can be sufficiently carried out when an electric current is applied in such a manner as in Example 1.

Furthermore, the cycle test $B_1$ was carried out by using a citric acid salt buffer solution (pH 6.8), which was the same as that used in Example 1, instead of MENI SOAK. After the cycle test $B_1$ was carried out about 40 cycles, it was observed with naked eyes that this contact lens became cloudy.

From this result, when a direct current is applied to the solution with repeatedly reversing the positive electrode and the negative electrode, the cleaning effect of a contact lens is exhibited.

Example 2

A cycle test was carried out in the same manner as in Example 1 except that DC voltage of 15 V having an initial electric current of 0.045 A was applied to 7 ml of the electrolyte solution used in the Referential Example 6 and an electric current was applied to the solution with repeatedly reversing a positive electrode and a negative electrode at the interval of time of 7.5 seconds in one direction and 1 minute in the opposite direction by using a reverse circuit (hereinafter referred to as cycle test $C_1$). After 40 minutes passed from the application of electric current, the temperature of the solution attained to 60° C. and the current was increased to 0.08 A. After the cycle test $C_1$ was applied to the contact lens 100 cycles, the contact lens was observed with naked eyes. As a result, the contact lens had transparency quite equal to the contact lens to which cycle test $C_1$ was not applied.

The cross section of the contact lens was analyzed by an X-ray microanalyzer (commercially available from JOEL Co., under the trade name of JSM type 35) to examine the existence of sulfur after the cycle test $C_1$ was carried out 100 cycles. As a result, the existence of sulfur was not observed in the treated contact lens.

Comparative Example 2

The same manner as in Comparative Example 1 was carried out except that the electrolyte solution used in the Referential Example 6 was used instead of MENI SOAK in cycle test $B_1$ in which LIZER E was employed (hereinafter referred to as cycle test $D_1$).

After the cycle test $D_1$ was carried out about 30 cycles, it was observed with naked eyes that this contact lens became cloudy. As is clear from the above results, when a direct current was applied to the solution with reversing the positive electrode and the negative electrode so that the interval of time before reversing was not equal to the interval of time after reversing, the cleaning effect of the contact lens was exhibited.

Examples 3 and 4

Two soft contact lenses mainly composed of N,N-dimethyl acrylamide having a water content of about 70% were immersed in 1.5 ml of the same artificial tear fluid as used in Example 1 at 40° C. for 3 hours to adsorb protein in the soft contact lenses.

The above two soft contact lenses were taken out from the artificial tear fluid, and one of them was lightly washed with the same electrolyte solution as used in Referential Example 6 by fingers. After that, the contact lens was immersed in 4 ml of the electrolyte solution, and voltage of 24 V having an initial current of 0.1 A was applied to the electrolyte solution for 30 minutes so that the temperature of the electrolyte solution became 80° C. after 20 minutes passed and the temperature was kept to 80° C. for 10 minutes with a temperature controller. While the voltage of 24 V was applied to the electrolyte solution, the positive electrode and the negative electrode were repeatedly reversed at the interval of time of 30 seconds by using a reverse circuit (Example 3). Then, the electrolyte solution was allowed to cool to room temperature. The above procedure was counted as one cycle. After the above procedure was repeated 150 cycles, the contact lens was observed with naked eyes. As a result, after about 130 cycles were carried out, it was found that the contact lens became a little cloudy.

The above procedure was applied to the remained contact lens 150 times except that the positive electrode and the negative electrode were repeatedly reversed at the interval of time of 7.5 seconds in one direction and 60 seconds in the opposite direction (Example 4). As a result, the contact lens showed transparency like a contact lens to which the above procedure was not applied.

From this result, it was found that when an electric current was applied to a treating solution so that the interval of time before reversing became different from the interval of time after reversing, excellent cleaning effects are imparted to a contact lens.

Examples 5 to 6 and Comparative Example 3

Three soft contact lenses mainly composed of N-vinylpyrrolidone having a water content of about 78% were immersed in 40 ml of the same artificial tear fluid as used in Example 1 at 25° C. for 10 days. The artificial tear fluid was replaced with another new artificial tear fluid every day.

The above three lenses were taken out from the tear fluid, then one of them was immersed in 7 ml of the same electrolyte solution as used in Referential Example 6 as it is at about 20° C. for 3 hours (Comparative Example 3). Also, another lens was immersed in 7 ml of the same electrolyte solution as the above eletrolyte solution for 3 hours, and voltage of 15 V having an initial current of 0.045 A was applied to the solution with repeatedly reversing the positive electrode and the negative electrode at the interval of time of 30 seconds by using a reverse circuit (Example 5). In this case, the period of time for the application of electric current was 10 minutes.

On the other hand, the remained lens was immersed in 7 ml of the same electrolyte solution as the above electrolyte solution, and the voltage of 15 V was applied to the solution for 10 minutes with repeatedly reversing the positive electrode and the negative electrode at the interval of time of 7.5 seconds in one direction and 1 minute in the opposite direction (Example 6). In this case, the period of time for the application of electric current was also 10 minutes.

Next, each lens was immersed in 10 ml of 1% amido black 10B staining solution (7% acetic acid aqueous solution) for 1 hour. After that, each lens was cleaned with 7% acetic acid aqueous solution 5 times. In this cleaning treatment, 100 ml of 7% acetic acid aqueous solution was used for each cleaning operation and the solution was exchanged for a new solution per 10 minutes. After cleaning, the lens was cleaned by immersing in methanol 5 times. In this cleaning treatment, 100 ml of methanol was used for each cleaning operation and the methanol was exchanged for a new methanol per 30 minutes.

The lens was further immersed in 100 ml of fresh methanol for one day. Then, each lens was again immersed in 50 ml of 7% acetic acid aqueous solution.

The colors of the three lenses were observed. As a result, the lens which was treated in Example 6 was not colored at all. On the other hand, the lens which was treated in Example 5 was slightly colored in blue and the lens which was treated in Comparative Example 3 was colored in brilliant blue, respectively. The degree of such blue coloration shows the amount of protein which is contained in the lens.

From this result, it was found that the method comprising applying an electric current to a treating solution with repeatedly reversing a positive electrode and a negative electrode so that the interval of time before reversing is different from the interval of time after reversing, is suitable for obtaining the effect of electrophoresis to electrically remove protein from the interior of the lens.

Example 7 and Comparative Example 4

A used cloudy contact lens was divided into three pieces. After two of the pieces were observed in a dark field with a microscope, respectively, the one was immersed in 7 ml of the electrolyte solution used in Referential Example 1 and voltage of 25 V having an initial electric current of 0.048 A was applied thereto for 30 minutes. At this time, a positive electrode and a negative electrode were repeatedly reversed at the interval of time of 30 seconds by using a reverse circuit (Example 7). After 30 minutes passed from the beginning of the application of electric current, the temperature of this solution attained to 70° C.

Then, another piece was immersed in 7 ml of the same electrolyte solution as the above, the solution was slowly boiled so that the temperature of the solution attained to 70° C. after 30 minutes (Comparative Example 4).

After the treatments, when the above two pieces of the lens were dried and observed in a dark field with a microscope, stains of the one which was treated by applying a direct current to the solution with repeatedly reversing a positive electrode and a negative electrode (Example 7), were almost removed, but stains of another which was merely boiled in the electrolyte solution (Comparative Example 4), were not entirely removed.

From the above results, it is found that peroxides generated by electrode reaction are effective for removing denatured and undissolved proteins.

Comparative Example 5

After remained unused one of three pieces of the returned cloudy contact lens which was divided in Example 7 and comparative Example 4 was observed in a dark field with a microscope, the piece was dipped in an agent for removing proteins HYDROCARE-F (commercially available from SANTEN-ALLERGAN, trade name) for 30 minutes.

After the above contact lens piece was dried, the piece was observed in a dark field with a microscope. As a result, no stains were almost removed from the piece.

As is clear from the comparison between the above contact lens piece and the contact lens of Example 7 in which the treatment time was the same (30 minutes), it can be seen that the treatment in Example 7 of the present invention can remove stains from a contact lens in an extremely shortened period of time.

Example 8 and Comparative Example 6

The same experiment as in Example 7 was repeated except that voltage of 15 V having an initial current of 0.045 A was applied to the same electrolyte solution as used in Referential Example 6 with repeatedly reversing a positive electrode and a negative electrode at the interval of time of 7.5 seconds in one direction and 1 minute in the opposite direction for 40 minutes by using a reverse circuit (Example 8). After 40 minutes passed from the beginning of the application of electric current, the temperature of this solution attained to 60° C.

After another piece was immersed in 7 ml of the same electrolyte solution as used in Referential Example 6, the solution was slowly boiled so that the temperature of the solution attained to 60° C. after 40 minutes (Comparative Example 6). After the treatments, when the above two pieces of the contact lens were dried and observed in a dark field with a microscope, stains of the one which was treated by applying a direct current to the solution with repeatedly reversing a positive electrode and a negative electrode (Example 8) were almost removed, but stains of another piece which was merely boiled in the electrolyte solution (Comparative Example 6) were not entirely removed.

From the above results, it is found that peroxides generated by electrode reaction are effective for removing denatured and undissolved proteins.

Examples 9 to 10 and Comparative Example 7

Three soft contact lenses mainly composed of hydroxylethyl methacrylate having a water content of about 30% were immersed in about 1.5 ml of the same artificial tear fluid as used in Example 1 at 25° C. for about 5 to 10 minutes to adsorb protein in the contact lens, and the artificial tear fluid was boiled for about 20 to 30 minutes. After that, the soft contact lenses were lightly rubbed by fingers to remove excess protein from the soft contact lenses and rinsed with saline. The above procedure was repeated 7 times to obtain artificially clouded lenses. After that, one of the obtained artificially clouded lenses was immersed in, 4 ml of the same electrolyte solution as used in Referential Example 6, and voltage of 24 V having an initial current of 0.1 A was applied to the electrolyte solution for 30 minutes in the same manner as in Example 3 so that the temperature of the electrolyte solution became 80° C. after 20 minutes passed and the temperature was kept to 80° C. for 10 minutes with a temperature controller. At that time, the positive electrode and the negative electrode were repeatedly reversed at the interval of time of 30 seconds (Example 9).

Another artificially clouded lens was treated in the same manner as in Example 9 except that the positive electrode and the negative electrode were repeatedly reversed at the interval of time of 7.5 seconds in one direction and 60 seconds in the opposite direction (Example 10).

Also, the remained artificially clouded lens was treated in the same manner as in Example 9 except that the positive electrode and the negative electrode were not reversed (Comparative Example 7).

In each of Examples 9 to 10 and Comparative Example 7, the treatment was carried out 3 times, and then the treated artificially clouded lens was observed by naked eyes with a stereomicroscope.

As a result, stains were remarkably removed from the two artificially clouded lenses to which an electric current was applied with reversing the positive electrode and the negative electrode.

To the contrary, stains were not removed from the artificially clouded lens to which an electric current was applied without reversing the positive electrode and the negative electrode.

Example 11

Four soft contact lenses mainly composed of N-vinylpyrrolidone having a water content of about 70% were immersed in 1.5 ml of an artificial tear fluid composed of the following components at, 37° C. for one hour.

| (Ingredients of the artificial tear fluid) | |
| --- | --- |
| Albumin | 11.64 g |
| γ-Globulin | 4.83 g |
| Lysozyme | 3.6 g |
| NaCl | 9.0 g |
| $CaCl_2.2H_2O$ | 0.15 g |
| $NaH_2PO_4.2H_2O$ | 1.04 g |
| Distilled water | 1.0 l |
| | (pH 7.0) |

Next, after two of the above contact lenses were cleaned by fingers with MENI CLEAN, the contact lenses were immersed in 8 ml of a 0.05 mol/l phosphoric acid salt buffer solution containing 0.2 mol/l of urea (pH 6.8), and voltage of 15 V having an initial current of 0.12 A was applied to the solution with repeatedly reversing a positive electrode and a negative electrode at the interval of time of 1 minute by using a reverse circuit for 30 minutes. After 30 minutes passed from the beginning of the application of electric current, the temperature of the solution attained to about 70°

C. During that procedure, the current value was increased up to 0.25 A. The solution was allowed to stand to cool to room temperature.

Next, the above procedure was counted as one cycle (hereinafter referred to cycle test $A_2$). After the procedure was applied to the contact lenses 100 cycles, the contact lenses were observed with naked eyes. As a result, the contact lenses had quite the same transparency as the contact lens which was not treated by the cycle test $A_2$.

Furthermore, when the cycle test $A_2$ was applied to the contact lenses 100 cycles, and the existence of sulfur and phosphorus in the cross section of the contact lens was examined by an X-ray microanalyzer, none of sulfur and phosphorus were detected.

From this result, it can be seen that the protein was removed when an electric current was applied to the solution.

Comparative Example 8

After two remained lenses of the four soft contact lenses which were treated with the artificial tear fluid in Example 11 were cleaned by fingers with MENI CLEAN, the soft contact lenses were disinfected by boiling in 1.5 ml of MENI SOAK with LIZER E.

Hereinafter, a cycle test (boiling was carried out using LIZER E instead of applying an electric current (hereinafter referred to as cycle test $B_2$)) was carried out 100 cycles in the same manner as in Example 11. As a result, it became obvious by naked eyes that the two contact lenses were cloudy after the cycle test $B_2$ was applied to the two contact lenses which were boiled in LIZER E about 20 cycles. Further, after the cycle test $B_2$ was carried out 100 cycles, the existence of sulfur and phosphorus was examined by an X-ray microanalyzer in the same manner as in Example 3. As a result, a peak showing the existence of sulfur was detected.

It is supposed that the cloudiness of this contact lens was caused by proteins, and when the contact lens was not electrically treated like the present invention, it can be seen that proteins are accumulated in the contact lens.

Also, a peak showing the existence of phosphorus was not detected.

Examples 12 to 20

Instead of a 0.05 mol/l phosphoric acid salt buffer solution (pH 6.8) containing 0.2 mol/l of urea used in Example 11 as an electrolyte solution, an electrolyte solution containing a component in a concentration shown in Table 2 was used, and the cycle test $A_2$ was applied 100 cycles to the same contact lenses as those used in Example 11 in the same manner as in Example 11. Also, the reverse of polarity of the electrodes was repeatedly carried out at the intervals of time shown in Table 2. Next, the transparency of the contact lenses was compared with that of the contact lenses which were not treated by the above cycle test $A_2$ with naked eyes. The results are shown in Table 2.

TABLE 2

| Example No. | Urea, thiocyanic acid salt and/or compound having reducing property contained in electrolyte solution | | Electrolyte contained in electrolyte solution | |
|---|---|---|---|---|
| | Kind | Concentration (mol/l) | Kind | Concentration (mol/l) |
| 12 | Urea | 0.15 | Sodium sulfate | 0.04 |
| 13 | Urea | 0.2 | Ammonium sulfate | 0.038 |
| 14 | Urea | 0.2 | Sodium acetate | 0.061 |
| 15 | Sodium sulfite | 0.03 | Sodium dihydrogenphosphate | 0.025 |
| | | | Disodium hydrogenphosphate | 0.025 |
| 16 | Sodium sulfite | 0.05 | Sodium dihydrogenphosphate | 0.025 |
| | | | Disodium hydrogenphosphate | 0.025 |
| 17 | Cysteine | 0.005 | Citric acid | 0.013 |
| | Sodium sulfite | 0.04 | Borax | 0.020 |
| 18 | Cysteine | 0.01 | Boric acid | 0.018 |
| | Sodium sulfite | 0.04 | Borax | 0.0013 |
| | | | Sodium citrate | 0.015 |
| 19 | Sodium thiocyanate | 0.02 | Potassium dihydrogenphosphate | 0.025 |
| | | | Disodium hydrogenphosphate | 0.025 |
| 20 | Urea | 0.1 | Boric acid | 0.015 |
| | | | Borax | 0.0011 |
| | | | Sodium citrate | 0.011 |

| Example No. | Interval of time of reversing the polarity of electrodes (second) | Voltage (V) | Transparency of lens after 100 cycles |
|---|---|---|---|
| 12 | 15 | 15 | Transparent |
| 13 | 60 | 20 | Transparent |
| 14 | 120 | 18 | Transparent |
| 15 | 30 | 20 | Transparent |
| 16 | 60 | 15 | Transparent |
| 17 | 30 | 15 | Transparent |
| 18 | 30 | 25 | Transparent |
| 19 | 60 | 15 | Transparent |
| 20 | 30 | 20 | Transparent |

As is clear from the results shown in Table 2, it can be seen that removal of proteins was carried out as to any of the contact lenses to which the cycle test $A_2$ was applied 100 cycles in Examples 12 to 20. Also, although the existence of sulfur and phosphorus in the cross section of the contact lenses was examined with an X-ray microanalyzer in the same manner as in Example 11, sulfur and phosphorus were not detected in any of the contact lenses used in Examples 12 to 20.

Example 21

The same procedure as in Example 11 was repeated except that voltage of 15 V having an initial current of 0.045 A was applied to the same electrolyte solution as used in Referential Example 7 with repeatedly reversing a positive electrode and a negative electrode at the interval of time of 7.5 seconds in one direction and 2 minutes in the opposite direction for 40 minutes by using a reverse circuit (Example 21). After 40 minutes passed from the beginning of the application of electric current, the temperature of this solution attained to about 65° C. During that procedure, the current value was increased up to 0.14 A.

After the above procedure (hereinafter referred to cycle test $C_2$) was applied to the contact lens 100 cycles, the contact lens was observed with naked eyes. As a result, the contact lens had quite the same transparency as the contact lens which was not treated by the cycle test $C_2$. Frthermore, after the cycle test $C_2$ was applied to the contact lens 100 cycles, the existence of sulfur and phosphorus in the cross section of the contact lens was examined by using an X-ray microanalyzer. As a result, none of sulfur and phosphorus were detected.

From these results, it is found that proteins were removed from the contact lens when an electricity was applied to the solution.

Examples 22 to 28

Instead of the 0.05 mol/l phosphoric acid salt buffer solution (pH 6.8) containing 0.2 mol/l of urea used in Example 21 as an electrolyte solution, each electrolyte solution containing a component in a concentration shown in Table 3 was used, and the cycle test $C_2$ was applied 100 cycles to the same contact lenses as those used in Example 21 in the same manner as in Example 21. Also, the polarity of the electrodes was repeatedly reversed at the interval of time shown in Table 3. Next, the transparency of the contact lenses was compared with that of the contact lenses which were not treated by the above cycle test $C_2$ with naked eyes. The results are shown in Table 3.

TABLE 3

| Example No. | Urea, thiocyanic acid salt and/or compound having reducing property contained in electrolyte solution | | Electrolyte contained in electrolyte solution | |
|---|---|---|---|---|
| | Kind | Concentration (mol/l) | Kind | Concentration (mol/l) |
| 22 | Urea | 0.15 | Sodium sulfate | 0.04 |
| 23 | Urea | 0.2 | Ammonium sulfate | 0.038 |
| 24 | Urea | 0.2 | Sodium acetate | 0.061 |
| 25 | Sodium sulfite | 0.03 | Sodium dihydrogenphosphate | 0.025 |
| | | | Disodium hydrogenphosphate | 0.025 |
| 26 | Sodium sulfite | 0.05 | Sodium dihydrogenphosphate | 0.025 |
| | | | Disodium hydrogenphosphate | 0.025 |
| 27 | Sodium thiocyanate | 0.02 | Potassium dihydrogenphosphate | 0.025 |
| | | | Disodium hydrogenphosphate | 0.025 |
| 28 | Urea | 0.1 | Boric acid | 0.015 |
| | | | Borax | 0.0011 |
| | | | Sodium citrate | 0.011 |

| Example No. | Interval of time of reversing the polarity of electrodes (second) | | Voltage (V) | Transparency of lens after 100 cycles |
|---|---|---|---|---|
| | To one direction | To opposite direction | | |
| 22 | 15 | 60 | 15 | Transparent |
| 23 | 30 | 120 | 20 | Transparent |
| 24 | 60 | 120 | 18 | Transparent |
| 25 | 15 | 120 | 20 | Transparent |
| 26 | 7.5 | 30 | 15 | Transparent |
| 27 | 15 | 60 | 15 | Transparent |
| 28 | 7.5 | 60 | 20 | Transparent |

Example 29

After two contact lenses which were similar to those used in Example 11 were immersed in 1.5 ml of the same artificial tear fluid as used in Example 11 at 37° C. for one hour, and the contact lenses were washed by fingers with MENI CLEAN, the contact lenses were disinfected in 1.5 ml of a 0.05 mol/l phosphoric acid salt buffer solution (pH 6.8) containing 0.2 mol/l of urea with LIZER E. Next, the above two contact lenses were allowed to stand to cool to room temperature.

The above procedure was counted as one cycle, and the procedure was applied to the above two contact lenses 50 cycles. When the contact lenses were observed with naked eyes, both contact lenses became cloudy after the above procedure was carried out 10 cycles or so.

From the above result, it can be seen that proteins cannot be removed from the contact lenses when the above disinfecting treatment using the LIZER E is carried out.

Furthermore, after the above treatment was carried out 50 cycles, one of the clouded contact lenses was immersed in 8 ml of a 0.05 mol/l phosphoric acid salt buffer solution (pH 6.8) containing 0.05 mol/l of sodium sulfite, and voltage of 18 V having an initial current of 0.12 A was applied to the solution with repeatedly reversing a positive electrode and a negative electrode at the interval of time of 2 minutes for 30 minutes by using a reverse circuit. After 30 minutes passed from the beginning of the application of electric current, the temperature of this solution attained to about 70° C., at which the current value was 0.25 A. After that, the contact lens was taken out from the solution. When the contact lens was examined with naked eyes, the contact lens was recovered to transparency.

From the above results, it can be seen that even though proteins are fixly adhered to contact lenses due to thermal denaturation, the proteins can be removed from the contact lenses by immersing the contact lenses in an electrolyte solution and applying a direct current to the solution with repeatedly reversing a positive electrode and a negative electrode according to the treating method of the present invention.

Example 30 and Comparative Example 9

To two of four soft contact lenses mainly composed of N-vinylpyrrolidone and N,N-dimethylacrylamide having a water content of 80%, the cycle test $A_2$ was applied 100 cycles in the same manner as in Example 11 (Example 30), and to the other two contact lenses, a treatment was applied in the same manner as in Comparative Example 11 (Comparative Example 9). After that, the cloudiness of contact lenses was observed.

The two contact lenses electrically treated in Example 30 were transparent after the cycle test $A_2$ was carried out 100 cycles. To the contrary, it was observed that the two contact lenses thermally treated by boiling with LIZER E in Comparative Example 9 became cloudy after the treatment was carried out 30 cycles or so.

Example 31 and Comparative Example 10

To two of four soft contact lenses mainly composed of N-vinylpyrrolidone and N,N-dimethylacrylamide having a water content of 72%, the cycle test $A_2$ was applied in the same manner as in Example 5 (Example 31), and to the other two contact lenses, a treatment was applied in the same manner as in Comparative Example 1 (Comparative Example 10). After that, the cloudiness of contact lenses was observed.

The two contact lenses electrically treated in Example 31 were transparent after the cycle test $A_2$ was carried out 100 cycles. To the contrary, it was observed that the two contact lenses treated by boiling with LIZER E in Comparative Example 10 became cloudy after the treatment was carried out 42 cycles or so.

Example 32

Two colored soft contact lenses of OPTIMA 38 (commercially available from BAUSCH & LOMB INCORPORATED, trade name) and HYDRON colored soft contact lens (commercially available from HYDRON JAPAN K.K., trade name: 114 Rodhos) were divided into two pieces with a razor's edge, respectively, and each of the two pieces was immersed to store in a saline. The remained pieces were immersed in 8 ml of the citric acid salt buffer solution (pH 6.8) used in Example 1, and DC voltage of 15 V having an initial current of 0.05 A was applied thereto for 30 minutes. After 30 minutes passed from the beginning of the application of electric current, the temperature of the solution attained to about 65° C., and the current value was increased to 0.11 A. The treatment was repeated. Also, during the treatment, the positive electrode and the negative electrode were repeatedly reversed at the interval of time of 30 seconds by using a reverse circuit, and the above buffer solution was exchanged for a new buffer solution per 30 minutes.

The treatment was applied to the pieces 365 times and the pieces were taken out from the treating solution. The degree of discoloration of the pieces was examined by comparing with the pieces stored in saline. As a result, the electrically treated pieces were not discolored at all.

From this result, it could be seen that the treating method of the present invention could be sufficiently applied to colored soft contact lenses.

Comparative Example 11

Two colored soft contact lenses of OPTIMA 38 and HYDRON colored soft contact lens which were the same as those used in Example 32 were divided into two pieces, respectively in the same manner as in Example 32, and each of the two pieces was immersed to store in a saline.

On the other hand, each of the remained pieces was immersed in 3.0 ml of an aqueous solution containing trisodium citrate in a content of 0.019 mol/l, citric acid in a content of 0.0003 mol/l and sodium chloride in a content of 0.154 mol/l and having a temperature of about 20° C., and an electric current of 0.006 A was applied thereto for 25 seconds with the same apparatus as used in Example 1. Thereby, about 5 ppm of sodium hypochlorite was generated in the aqueous solution to disinfect. After the solution was allowed to stand for 60 minutes at room temperature as it was, each of the pieces was taken out, and the above solution was exchanged for a new solution. The procedure was counted as one cycle, and the cycle was repeated 50 times.

The degree of discoloration or decoloration of the contact lenses was observed by comparing the color of the disinfected pieces with the color of the same type of pieces stored in a saline in the same manner as described in the above. As a result, the pieces of the colored soft contact lenses of BAUSCH & LOMB were completely decolored when the above procedure was only 2 cycles repeated. It was also observed that the pieces of the colored soft contact lens of HYDRON was discolored after the procedure was repeated 20 cycles.

From the above results, when a disinfecting system comprising treating a colored soft contact lens with a hypohalogenous acid salt was employed, it could be seen that the colored soft contact lens was discolored or decolored.

Example 33 and Comparative Example 12

Each of two oxygen-permeable hard contact lenses "MENICON EX" (commercially available from Menicon Co., Ltd., trade name) was boiled in 1.5 ml of the same artificial tear fluid as used in Example 1 for 10 minutes to adhere stains of protein to the contact lens.

Then, one of them was immersed in 8 ml of the electrolyte solution which was used in Example 26, and voltage of 15 V having an initial current of 0.15 A was applied to the solution with repeatedly reversing a positive electrode and a negative electrode at the interval of time of 30 seconds by using a reverse circuit.

After 20 minutes passed from the beginning of the electrical treatment, the temperature of this solution attained to about 45° C. During the treatment, the current value was increased to 0.20 A (Example 33).

Another was immersed in an agent for removing proteins, HYDROCARE-F for 20 minutes (Comparative Example 12).

After each contact lens was taken out and washed with tap water, respectively, the contact lens was dried and observed in a dark field with a microscope. As a result, stains were almost removed from the contact lens in Example 33, but stains were little removed from the contact lens in Comparative Example 12.

As is clear from the comparison between Example 33 and Comparative Example 12 in which the contact lens was treated for the same period of time (20 minutes), it is found that according to Example 33, stains of contact lens can be effectively removed in a very short period of time.

Example 34 and Comparative Example 13

Four soft contact lenses mainly composed of hydroxylethyl methacrylate having a water content of about 38% were strongly held with a thumb and a forefinger to give the soft contact lenses oil stains.

The soft contact lenses were dried to fix the oil stains as they were, and photographs of the soft contact lenses were taken with a microscope.

Two of the soft contact lenses were held to every two holders. One holder was put on the electrode in a vessel (Example 34) and another holder was put on a portion away from the electrodes, where bubbles generated by electrolysis were not contacted with the soft contact lenses (Comparative Example 13). Then, the vessel was charged with 10 ml of an electrolyte solution (pH 6.7) containing boric acid in a content of 0.161 mol/l, borax in a content of 0.0009 mol/l and sodium phosphate in a content of 0.035 mol/l, and a direct current of 18 V having an initial current of 0.05 A was applied to the electrolyte solution with repeatedly reversing the positive electrode and the negative electrode at an interval of time of 3.75 seconds in one direction and 1 minute in another direction by using a reverse circuit to remove stains from the soft contact lenses. The period of time for applying the direct current was 40 minutes.

After the treatment, the soft contact lenses were dried again, and photographs of the soft contact lenses were taken with a microscope.

As a result, stains were completely removed from the soft contact lenses treated in Example 34. To the contrary, stains were remained a little on the soft contact lenses treated in Comparative Example 13.

As is clear from the above results, when bubbles generated by the electrolysis from the electrodes were contacted with the soft contact lenses, stains can be easily removed from the soft contact lenses.

Experiment 1 and Comparative Experiment 1 (Test for examining disinfecting properties)

Figure 4:
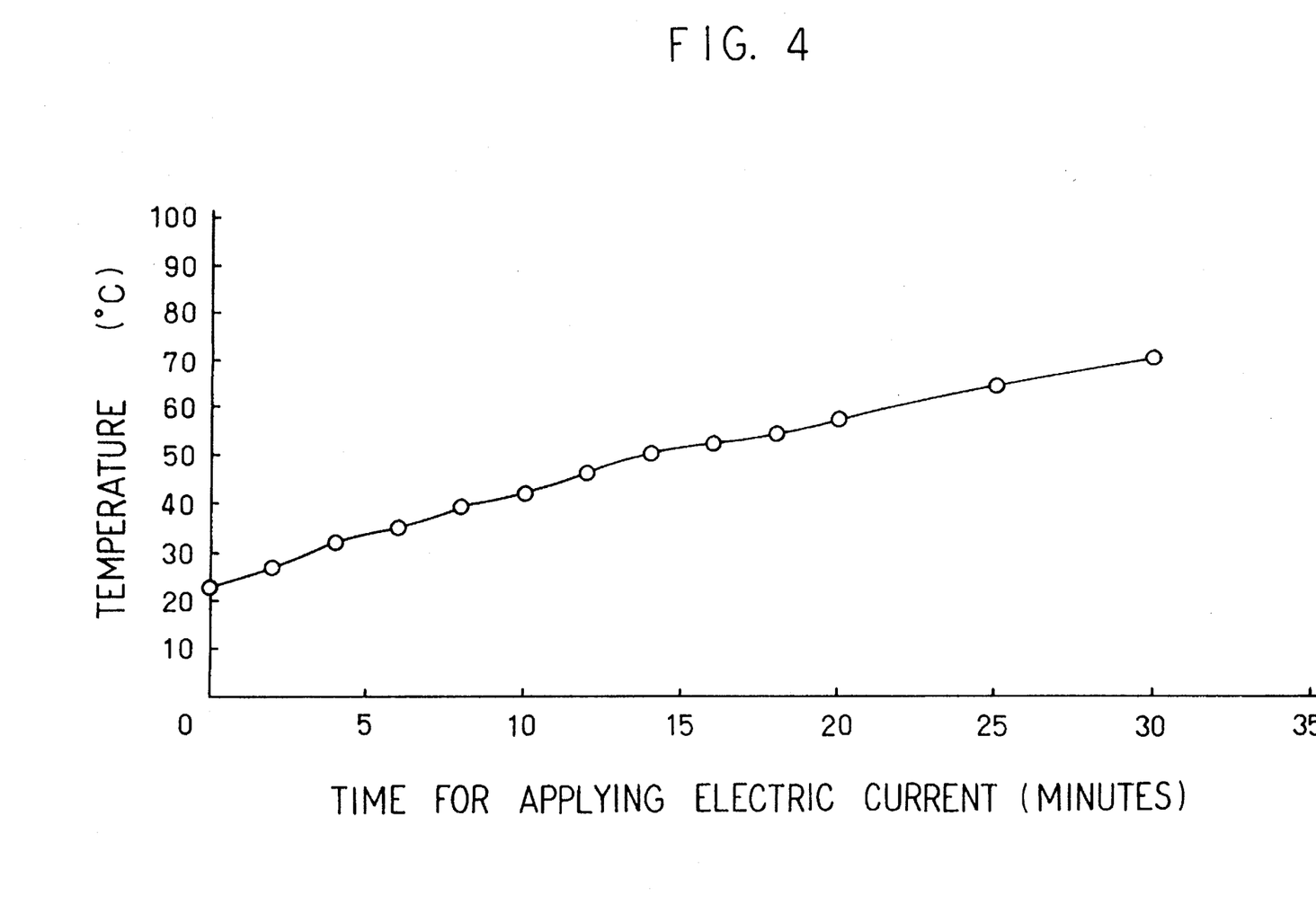
FIG. 4 is a graph showing the change of temperature of the electrolyte solution with the passage of time during the application of a direct current to the electrolyte solution to which a microbial suspension is added in Experiment 1 of the present invention and Comparative Experiment 1.

To 10 ml of the electrolyte solution used in Referential Example 1, 0.1 ml of liquid containing $1.2 \times 10^8$ cells/ml of Staphylococcus aureus or Pseudomonas aeruginosa was added, and the solution was treated by applying a direct current of 25 V having an initial current of 0.048 A for 30 minutes. The change of temperature of the electrolyte solution during the treatment is shown in FIG. 4. As to Experiment 1, the positive electrode and the negative electrode were repeatedly reversed at the interval of 30 seconds by using a reverse circuit. As to Comparative Experiment 1, the positive electrode and the negative electrode were not reversed.

After 30 minutes passed from the beginning of the application of electric current, 1.0 ml of the electrolyte solution was taken out and then added to 15 ml of fluid thioglycolate medium for sterility tests commercially available from EIKEN CHEMICAL CO., LTD.. After that, the microorganism was cultivated at 31° C. for 7 days, and disinfecting property was examined.

As a result, according to the results of Experiment 1, the growth of the above two microorganisms was not observed after 7 days passed, which shows that the reversing of the positive electrode and the negative electrode shows excellent disinfecting properties.

To the contrary, according to the results of Comparative Experiment 1, the growth of the above two microorganisms was observed after 1 day passed.

From the above results, it can be understood that sufficient disinfecting properties cannot be obtained when a direct current is merely applied to the electrolyte solution, and that sufficient disinfecting properties can be obtained when the positive electrode and the negative electrode are repeatedly reversed as is clear from the results of Experiment 1 because a great amount of peroxide is generated during the electrode reaction in comparison with a conventional method.

Experiment 2 and Comparative Experiment 2 (Test for examining disinfecting properties)

To 10 ml of the electrolyte solution used in Referential Example 1, 0.1 ml of water containing $1.5 \times 10^7$ cells/ml of Aspergills fumigatus or Candida albicans was added, and the water was treated by applying a direct current of 25 V having an initial current of 0.048 A for 30 minutes. As to Experiment 2, the positive electrode and the negative electrode were repeatedly reversed at the interval of 30 seconds. As to Comparative Experiment 2, the positive electrode and the negative electrode were not reversed.

After 30 minutes passed from the beginning of the application of electric current, 1.0 ml of the electrolyte solution was taken out and then added to 15 ml of dextrose peptone broth for sterility tests commercially available from EIKEN CHEMICAL CO., LTD.. After that, the microorganism was cultivated for 10 days at 25° C., and its disinfecting property was examined.

As a result, according to the results of Experiment 2, the growth of the above two microorganisms was not observed after 10 days passed, which shows that the reversing of the positive electrode and the negative electrode shows excellent disinfecting properties.

To the contrary, according to the results of Comparative Experiment 2, the growth of the above two microorganisms was observed after 3 days passed.

From the above results, it can be understood that a great amount of peroxide generated during the electrode reaction exhibits great disinfecting properties in comparison with a conventional method.

Experiment 3 and Comparative Experiment 3 (Test for examining disinfecting properties)

Figure 5:
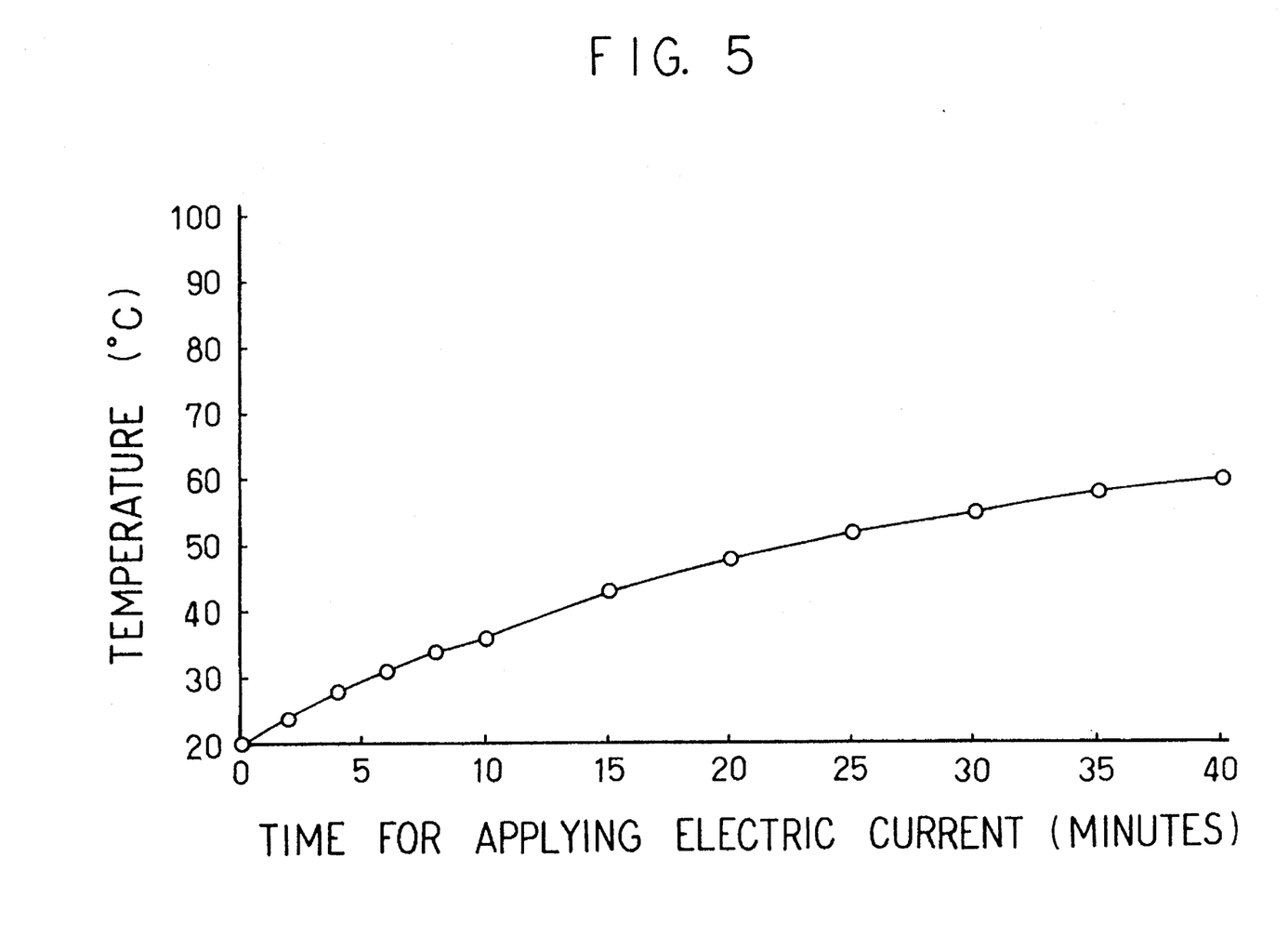
FIG. 5 is a graph showing the change of temperature of the electrolyte solution with the passage of time during the application of a direct current to the electrolyte solution to which a microbial suspension is added in Experiment 3 of the present invention and Comparative Experiment 3.

To 10 ml of the electrolyte solution used in Referential Example 6, 0.1 ml of liquid containing $1.2 \times 10^8$ cells/ml of Staphylococcus aureus or Pseudomonas aeruginosa was added, and the liquid was treated by applying a direct current of 15 V having an initial current of 0.045 A for 40 minutes. The change of the temperature of the electrolyte solution was shown in FIG. 5. As to Experiment 3, the positive electrode and the negative electrode were repeatedly reversed at the interval of 7.5 seconds in one direction and 1 minute in the opposite direction with a reverse circuit. As to Comparative Experiment 3, the positive electrode and the negative electrode were not reversed.

After 40 minutes passed from the beginning of the application of electric current, 1.0 ml of the electrolye solution was taken out and then added to fluid thioglycolate medium for sterility tests commercially available from EIKEN CHEMICAL CO., LTD.. After that, the microorganism was cultivated for 7 days, and disinfecting property was examined.

As a result, according to the results of Experiment 3, the growth of the above two microorganisms was not observed after 7 days passed, which shows that excellent disinfecting properties were exhibited by repeatedly reversing the positive electrode and the negative electrode so that the interval in one direction differs from that in another direction.

To the contrary, as to Comparative Experiment 3, the growth of the above two microorganisms was observed after 1 day passed.

Experiments 4 to 8 (Test for examining disinfecting properties)

In Experiment 4, phosphate buffer used in Referential Example 10 was used as an electrolyte solution and the applied voltage was adjusted to 17 V. In Experiment 5, borate buffer used in Referential Example 11 was used as an electrolyte solution and the applied voltage was adjusted to 25 V. In Experiment 6, citrate buffer used in Referential Example 12 was used as an electrolyte solution and the applied voltage was adjusted to 20 V. In Experiment 7, a sodium sulfate aqueous solution used in Referential Example 13 was used as an electrolyte solution and the applied voltage was adjusted to 15 V. In Experiment 8, a sodium hydrogencarbonate aqueous solution used in Referential Example 14 was used as an electrolyte solution and the applied voltage was adjusted to 10 V.

Other conditions than the above were controlled in the same manner as in Experiment 1, and the disinfecting properties for Staphylococcus aureus and Pseudomonas aeruginosa were examined. As a result, the growth of the above two microorganisms was not observed after 7 days passed as to all of Experiments 4 to 8, which shows that excellent disinfecting properties were exhibited.

Also, interval of time for changing electrodes, period of time for applying direct current, final temperature of solution and reversing times of electrodes in Examples 1 to 34 and Experimental Examples 1 to 3 are shown in Table 4.

TABLE 4

| Ex. No. | Interval of time for changing electrodes (second) | Period of time for applying direct current (second) | Final Temperature of solution (°C.) | Reversing times for electrodes (second) |
|---|---|---|---|---|
| 1 | 30 | 1800 | 75 | 60 |
| 2 | 7.5/60 | 2400 | 60 | 71 |
| 3 | 30 | 1800 | 80 | 60 |
| 4 | 7.5/60 | 1800 | 80 | 53 |
| 5 | 30 | 600 | | 20 |
| 6 | 7.5/60 | 600 | | 17 |
| 7 | 30 | 1800 | 70 | 60 |
| 8 | 7.5/60 | 2400 | 60 | 36 |
| 9 | 30 | 1800 | 80 | 60 |
| 10 | 7.5/60 | 2400 | 80 | 71 |
| 11 | 60 | 1800 | 70 | 30 |
| 12 | 15 | 1800 | 70 | 120 |
| 13 | 60 | 1800 | 70 | 30 |
| 14 | 120 | 1800 | 70 | 15 |
| 15 | 30 | 1800 | 70 | 60 |
| 16 | 60 | 1800 | 70 | 30 |
| 17 | 30 | 1800 | 70 | 60 |
| 18 | 30 | 1800 | 70 | 60 |
| 19 | 60 | 1800 | 70 | 30 |
| 20 | 30 | 1800 | 70 | 60 |
| 21 | 7.5/120 | 2400 | 65 | 38 |
| 22 | 15/60 | 2400 | 65 | 64 |
| 23 | 30/120 | 2400 | 65 | 32 |
| 24 | 60/120 | 2400 | 65 | 26 |
| 25 | 15/120 | 2400 | 65 | 36 |
| 26 | 7.5/30 | 2400 | 65 | 128 |
| 27 | 15/60 | 2400 | 65 | 64 |
| 28 | 7.5/60 | 2400 | 65 | 72 |
| 29 | 120 | 1800 | 70 | 15 |
| 30 | 60 | 1800 | 70 | 30 |
| 31 | 30 | 600 | | 20 |
| 32 | 30 | 1800 | 65 | 60 |
| 33 | 30 | 1200 | 45 | 40 |
| 34 | 3.75/60 | 2400 | 80 | 75 |
| Experimental Ex. | | | | |
| 1 | 30 | 1800 | 70 | 60 |
| 2 | 30 | 1800 | 70 | 60 |
| 3 | 7.5/60 | 1800 | 70 | 54 |

As is clear from the results shown in the above, according to the cleaning and disinfecting method of the present invention, since a peroxide is generated in a great high concentration in an electrolyte solution during electrode reaction, a contact lens can be effectively cleaned and disinfected.

In addition to the ingredients used in the Examples, other ingredients can be used in the Examples as set forth in the specification to obtain substantially the same results.

What is claimed is:

1. A method for cleaning and disinfecting a contact lens comprising the steps of:

A. immersing a contact lens in a treating solution, which does not generate hypohalogenous acid salts, selected from the group consisting of boric acid salt buffer solution, phosphoric acid salt buffer solution, citric acid salt buffer solution, acetic acid salt buffer solution, oxalic acid salt buffer solution, succinic acid salt buffer solution, tartaric acid salt buffer solution, an aqueous solution containing a treating agent of which main components are boric acid and borax, $Na_2SO_4$ aqueous solution and admixture thereof, B. applying a direct current to the treating solution with repeatedly reversing a positive electrode and a negative electrode of a pair of electrodes plural times so that the interval of time before reversing is different from the interval of time after reversing by at least 22.5 seconds and that the interval for reversing the positive electrode and the negative electrode is 0.1 second to 120 seconds, to generate hydrogen peroxide or ozone and raise the temperature of the treating solution to 50° to 100° C., and C. bringing the contact lens into direct contact with bubbles generated on the electrodes.

2. The method for cleaning and disinfecting a contact lens of claim 1, wherein the direct current applied is 0.001 to 0.5 A.

3. The method for cleaning and disinfecting a contact lens of claim 1, wherein pH of the treating solution is at a pH of 5.5 to 8.

4. The method for cleaning and disinfecting a contact lens of claim 1, wherein the content of an electrolyte in the treating solution is 0.001 to 0.5 mol/l.

\* \* \* \* \*